US008300913B2

(12) United States Patent
Yamaguchi et al.

(10) Patent No.: US 8,300,913 B2
(45) Date of Patent: Oct. 30, 2012

(54) APPARATUS AND METHOD FOR PROCESSING RADIATION IMAGE

(75) Inventors: Yoshitaka Yamaguchi, Minami-ashigara (JP); Sadato Akahori, Odawara (JP); Kazuharu Ueta, Tokyo (JP); Yasunori Ohta, Yokohama (JP); Atsushi Fukuda, Koganei (JP)

(73) Assignee: FUJIFILM Corporation, Tokyo (JP)

( * ) Notice: Subject to any disclaimer, the term of this patent is extended or adjusted under 35 U.S.C. 154(b) by 997 days.

(21) Appl. No.: 12/238,721

(22) Filed: Sep. 26, 2008

(65) Prior Publication Data

US 2009/0087069 A1   Apr. 2, 2009

(30) Foreign Application Priority Data

Sep. 27, 2007   (JP) ................................. 2007-252454

(51) Int. Cl.
*G06K 9/00* (2006.01)
*H05G 1/64* (2006.01)

(52) U.S. Cl. .............. 382/132; 382/131; 378/5; 378/54; 378/98.9

(58) Field of Classification Search .................. 382/130, 382/132; 378/5, 54, 98.11, 98.9
See application file for complete search history.

(56) References Cited

U.S. PATENT DOCUMENTS

| 3,848,130 | A | * | 11/1974 | Macovski | 378/98.9 |
|---|---|---|---|---|---|
| 3,904,874 | A | * | 9/1975 | Amtmann et al. | 378/98.9 |
| 4,233,507 | A | * | 11/1980 | Volz | 378/18 |
| 4,463,375 | A | * | 7/1984 | Macovski | 378/98.12 |
| 4,773,086 | A | * | 9/1988 | Fujita et al. | 378/4 |
| 5,335,260 | A | * | 8/1994 | Arnold | 378/207 |
| 6,501,819 | B2 | | 12/2002 | Unger et al. | |
| 6,643,536 | B2 | | 11/2003 | Nicolas et al. | |
| 6,683,934 | B1 | * | 1/2004 | Zhao et al. | 378/9 |
| 7,712,961 | B2 | * | 5/2010 | Horndler et al. | 378/207 |
| 2003/0048867 | A1 | * | 3/2003 | Acharya et al. | 378/18 |
| 2005/0135558 | A1 | * | 6/2005 | Claus et al. | 378/42 |
| 2006/0062448 | A1 | * | 3/2006 | Hirsch et al. | 382/154 |

FOREIGN PATENT DOCUMENTS

| JP | 2002-325756 A | 11/2002 |
|---|---|---|
| JP | 2002-330954 A | 11/2002 |

* cited by examiner

*Primary Examiner* — Alexander H Taningco
(74) *Attorney, Agent, or Firm* — Sughrue Mion, PLLC

(57) ABSTRACT

A radiation image processing apparatus includes a radiation source for irradiating the subject with the radiation, the subject being applied with a fixation material, a radiation source controller for controlling the radiation source in accordance with different image capturing conditions, a radiation converting panel for converting the radiation into one of the pieces of radiation image information, a processing condition memory for storing a plurality of processing conditions, each including the image capturing conditions that correspond to a type of the fixation material, a processing condition selector for selecting one of the processing conditions, the selected one of the processing conditions corresponding to the type of the fixation material, and an image processor for processing in accordance with the selected processing condition the plurality of pieces of radiation image information that are provided by the radiation converting panel under the different image capturing conditions, respectively.

10 Claims, 4 Drawing Sheets

FIG. 2

| PROCESSING CONDITION | TYPE OF FIXTURE MATERIAL | IMAGE CAPTURING SITE | FIRST IMAGE CAPTURING CONDITION ($S_1$) | SECOND IMAGE CAPTURING CONDITION ($S_2$) | WEIGHTING COEFFICIENT ($\alpha$) |
|---|---|---|---|---|---|
| A | PLASTER | KNEE | 50kVp/20mAs | 120kVp/6mAs | −0.45 |
| B | PLASTER | ARM | 60kVp/20mAs | 120kVp/6mAs | −0.45 |
| C | FIBERGLASS | KNEE | 50kVp/20mAs | 120kVp/6mAs | −0.6 |
| D | FIBERGLASS | ARM | 60kVp/20mAs | 120kVp/6mAs | −0.6 |

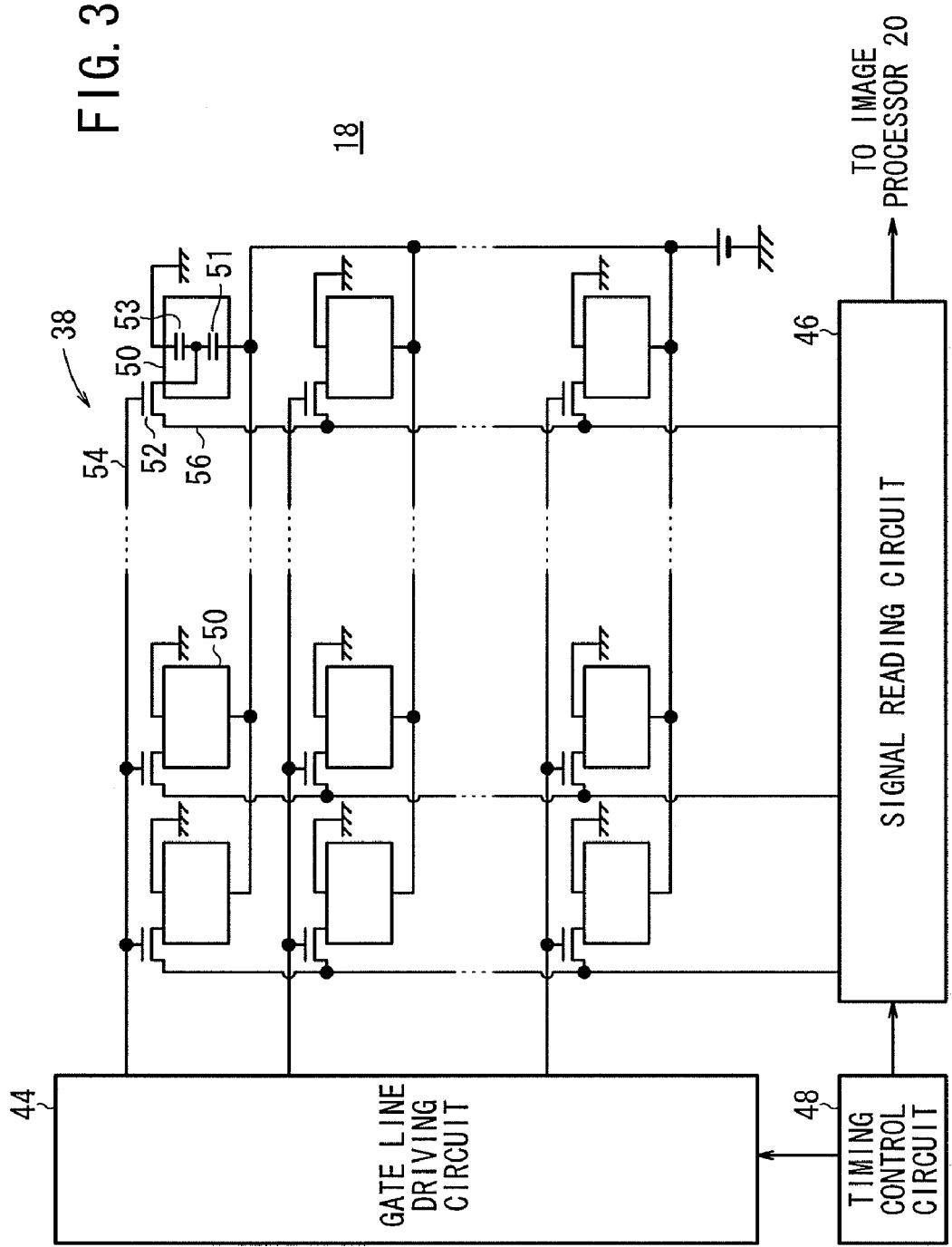

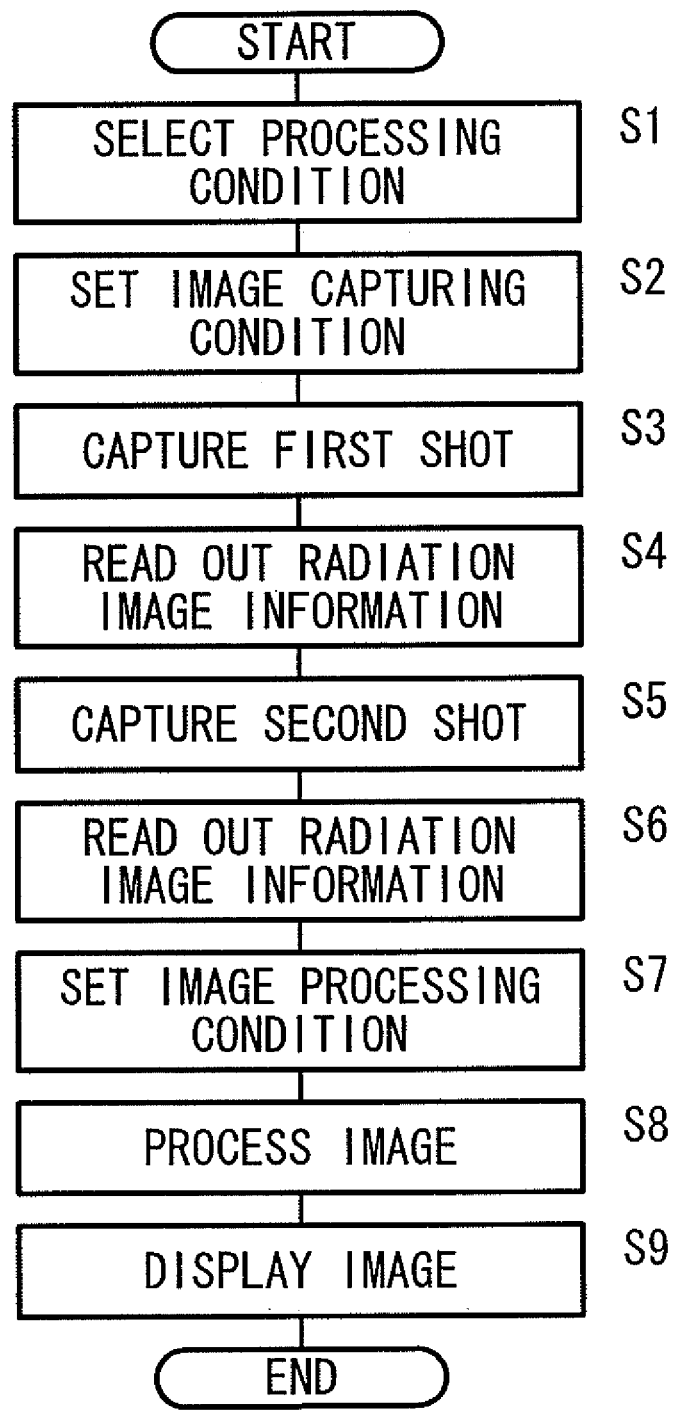

APPARATUS AND METHOD FOR PROCESSING RADIATION IMAGE

BACKGROUND OF THE INVENTION

1. Field of the Invention

The present invention relates to a radiation image processing apparatus and a processing method for producing a piece of radiation image information of a desired image capturing site by processing a plurality of pieces of radiation image information acquired by applying radiation of different energies to a subject, respectively.

2. Description of the Related Art

In the medical field, for example, extensive use is made of radiation image processing apparatuses which expose a subject (patient) to radiation emitted from a radiation source, guide the radiation that has passed through the subject to a radiation converting panel for converting radiation into radiation image information, and then perform predetermined image processing on the radiation image information. Processed radiation image information is displayed on a display unit and can be used for diagnosis etc.

One example of the radiation converting panel is a solid-state detector that converts radiation into charge information and stores the charge information so that it can be read out as an electric signal. Another example of the radiation converting panel is a stimulable phosphor panel. The stimulable phosphor panel stores radiation energy in a phosphor and emits stimulated light of an intensity corresponding to the stored energy when irradiated with stimulating light such as a laser beam.

One practical application of the radiation image apparatus is the extraction of a region of interest in the subject, e.g., soft tissue such as the heart and lungs located under ribs, from the radiation image information. The extraction of the region of interest is achieved based on a difference in absorption characteristics between bone such as the ribs, and soft tissue such as the heart. Radiation of different energies is applied to the subject using two different image capturing conditions to acquire two pieces of radiation image information. The extraction of the bone or soft tissue of interest is achieved by computing the difference between the two pieces of radiation image information after weighting with one or more predetermined coefficients (see Japanese Laid-Open Patent Publication No. 2002-325756).

Different internal structures of the subject have different radiation absorption characteristics. Therefore, it is necessary to process the image in accordance with these characteristics to acquire a proper image of the region of interest. For example, if the subject is a fracture that is applied with a fixture material such as a plaster cast, the image processing should take into consideration the radiation absorption characteristics of the plaster and bones.

The image processing method disclosed in Japanese Laid-Open Patent Publication No. 2002-330954, acquires a first piece of radiation image information by applying radiation to a subject in accordance with a predetermined image capturing condition. Then, the image capturing condition is modified based on analysis of the first piece of radiation image information, and used for acquisition of a second piece of radiation image information. Finally, an image of a region of interest is produced from the first and second pieces of radiation image information.

However, the method disclosed in Japanese Laid-Open Patent Publication No. 2002-330954, which determines the image capturing condition for the second piece of radiation image information based on the first piece of radiation image information, may fail to obtain proper image information when the subject moves before the acquisition of the second piece of radiation image information.

The fixture material applied to the subject can be plaster of a plaster cast or fiberglass, which have different radiation absorption characteristics. If plaster is used, the radiation absorption characteristic is also affected by the water content of the plaster, which decreases with solidification. The radiation absorption of the plaster cast with some water content at the beginning of application is different from that of the plaster cast which is solidified after a certain time. Therefore, it is necessary to process the pieces of radiation image information with consideration for the radiation absorption characteristics of the subject. Japanese Laid-Open Patent Publication No. 2002-330954, however, does not take into account the radiation absorption characteristics of the subject. Therefore, it may fail to acquire a proper image capturing condition from the first piece of radiation image information and determine suitable weighting coefficients for the weighted subtraction using the first and second pieces of radiation image information.

SUMMARY OF THE INVENTION

It is a general object of the invention to provide a radiation image processing apparatus and a processing method that are capable of acquiring suitable radiation image information of a desired image capturing site of a subject applied with a fixation material.

It is a main object of the invention to provide a radiation image processing apparatus and a processing method that are capable of acquiring suitable radiation image information of a subject applied with a fixation material without being affected by the subject's movement.

It is another object of the invention to provide a radiation image processing apparatus and a processing method that are capable of determining an appropriate image capturing condition for acquisition of suitable radiation image information of a subject applied with a fixation material.

BRIEF DESCRIPTION OF THE DRAWINGS

FIG. 2 illustrates a processing condition table stored in a processing condition memory of the radiation image processing apparatus of FIG. 1;

FIG. 3 is a block diagram illustrating a circuit configuration of a solid-state radiation detector according to an embodiment of the invention; and FIG. 4 is a flow chart illustrating the operation of the radiation image processing apparatus of FIG. 1.

DESCRIPTION OF THE PREFERRED EMBODIMENTS

Figure 1:
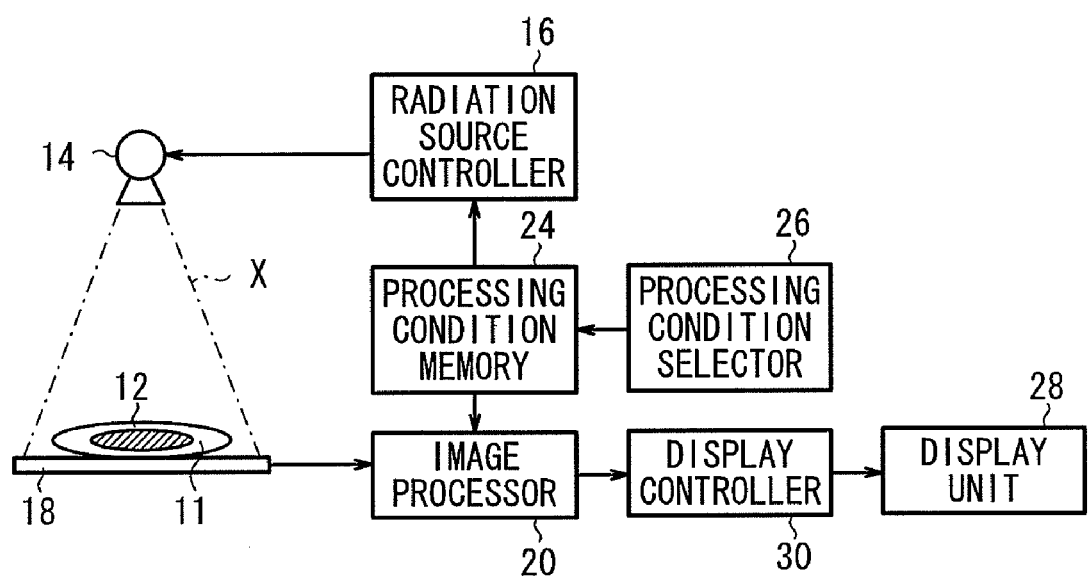
FIG. 1 is a block diagram illustrating a configuration of a radiation image processing apparatus according to an embodiment of the invention.

FIG. 1 is a block diagram illustrating a configuration of a radiation image processing apparatus 10 according to an embodiment of the invention.

The radiation image processing apparatus 10 includes a radiation source 14 for applying radiation X to a subject 12 applied with a fixation material 11 such as plaster or fiberglass, a radiation source controller 16 for controlling the radiation source 14 in accordance with predetermined image capturing conditions such as a tube voltage, a tube current, and irradiation time, and a solid-state radiation detector 18

(radiation converting panel) for converting the radiation X that has passed through the subject 12 into charge information serving as radiation image information. The radiation image processing apparatus 10 further includes an image processor 20 for processing the radiation image information detected by the solid-state radiation detector 18, a processing condition memory 24 for storing processing conditions including the above-mentioned image capturing conditions in the form of a processing condition table 22 shown in FIG. 2, and a processing condition selector 26 for retrieving from the processing condition memory 24 a processing condition required for producing desired radiation image information. The radiation image processing apparatus 10 also includes a display unit 28 for displaying the radiation image information processed by the image processor 20, and a display controller 30 for controlling the display unit 28.

The image processor 20 produces a piece of radiation image information of a desired image capturing site of the subject 12 applied with the fixation material 11. The image processor 20 is supplied with a plurality of pieces of radiation image information obtained by applying radiation of different energies to the subject 12, and produces the piece of radiation image information mentioned above by carrying out a weighted subtraction computed as $$S = \alpha \cdot S_1 + S_2$$

where S is the above-mentioned resultant piece of radiation image information, $S_1$ and $S_2$ are pieces of radiation image information obtained with first and second image capturing conditions, respectively, and $\alpha$ is a weighting coefficient.

In order to obtain an image of the desired image capturing site having suitable contrast and brightness, the weighted subtraction may alternatively be computed as $$S = K_1 \cdot S_1 + K_2 \cdot S_2 + K_3$$

where $K_1$, $K_2$ and $K_3$ are coefficients depending on the weighting coefficient for extraction of the desired image capturing site and the gradation characteristics of the first and second pieces of radiation image information $S_1$ and $S_2$.

FIG. 2 shows the processing condition table 22 stored in the processing condition memory 24. The processing condition table 22 includes a first image capturing condition ($S_1$), a second image capturing condition ($S_2$), and a weighting coefficient $\alpha$ corresponding to a type of the fixation material 11 applied to the subject 12 and an image capturing site. The first and second image capturing conditions ($S_1$) and ($S_2$) and the weighting coefficient $\alpha$ are determined so as to minimize exposure dose of the subject 12. Each of the first and second image capturing conditions ($S_1$) and ($S_2$) includes a tube voltage and a tube current to be set to the radiation source 14. In the present embodiment, the processing condition table 22 includes four processing conditions A through D. Processing conditions A through D represent the conditions required for extracting a knee applied with plaster as the fixation material 11, an arm applied with plaster as the fixation material 11, a knee applied with fiberglass as the fixation material 11, and an arm applied with fiberglass as the fixation material 11, respectively.

Note that the first and second image capturing conditions ($S_1$) and ($S_2$) may remain constant for all processing conditions, while varying the weighting coefficient $\alpha$ with the type of the fixation material 11 and the image capturing site. Conversely, a fixed weighting coefficient $\alpha$ may be used for all processing conditions, while varying the first and second image capturing conditions ($S_1$) and ($S_2$) with the type of the fixation material 11 and the image capturing site. If the fixation material 11 is plaster, the radiation absorption characteristic varies with the water content of the plaster, which is high at the beginning but decreases with time as the plaster solidifies. In such a case, the weighting coefficient $\alpha$ may be defined as a function of time after application of the fixation material 11 to the subject 12, i.e., $\alpha(t)$.

FIG. 3 is a block diagram illustrating a circuit configuration of the solid-state radiation detector 18. The solid-state radiation detector 18 includes a sensor substrate 38, a gate line driving circuit 44, a signal reading circuit 46, and a timing control circuit 48 that controls the gate line driving circuit 44 and the signal reading circuit 46.

The sensor substrate 38 includes a two-dimensional array of Thin Film Transistors (TFTs) 52 and a photoelectric conversion layer 51 disposed over the TFTs 52. The photoelectric conversion layer 51 is made of a material such as amorphous selenium (a-Se), which generates charge on sensing radiation X. The sensor substrate 38 stores the charge generated by the a-Se layer into storage capacitors 53. Then, the TFTs 52 in each row of the two-dimensional array are sequentially switched on to allow the charges of the storage capacitors 53 to be read out as image signals. FIG. 3 only shows the connection between one TFT 52 and one pixel 50 which is made up of one storage capacitor 53 and a corresponding part of the photoelectric conversion layer 51. The details of other pixels 50 are omitted for clarity. Note that the amorphous selenium shows performance degradation at high temperatures because of an inherent structural change and must therefore be used within a predetermined temperature range. The TFT 52 of each pixel 50 is connected to a gate line 54 extending in the row direction of the TFT array and a signal line 56 extending in the column direction of the TFT array. Each gate line 54 is connected to the gate line driving circuit 44, and each signal line 56 is connected to the signal reading circuit 46.

The radiation image processing apparatus 10 of the present embodiment is essentially configured as described above. The operation of the radiation image processing apparatus 10 will now be described with reference to the flow chart shown in FIG. 4.

First, an operator selects one of the processing conditions stored in the processing condition memory 24 using the processing condition selector 26 (step S1). If, for example, radiation image information of the knee of the subject 12 is required, and the fixation material 11 formed around the knee is plaster, the processing condition A is selected from the processing condition table 22 of the processing condition memory 24.

Next, the first and second image capturing conditions ($S_1$) and ($S_2$) of the selected processing condition are provided to the radiation source controller 16 (step S2).

A first shot is then captured by applying radiation to the subject 12 through the fixation material 11 with the radiation source controller 16 controlling the tube voltage and the tube current of the radiation source 14 in accordance with the first image capturing condition ($S_1$) (step S3).

The radiation X that has passed through the subject 12 and the fixation material 11 is converted into an electric signal by the photoelectric conversion layer 51 of each of the pixels 50 which make up the sensor substrate 38 of the solid-state radiation sensor 18. The electric signals are then stored into the storage capacitors-53 as charges. Then, the timing control circuit 48 supplies timing control signals to the gate line driving circuit 44 and the signal reading circuit 46 to allow readout from each storage capacitor 53 of the sensor substrate 38 the electrical information representing the first shot radiation image information $S_1$ of the subject 12.

More specifically, the gate line driving circuit 44 selects one of the gate lines 54 in accordance with the timing control signal provided by the timing control circuit 48 and supplies a driving signal to the base terminal of each TFT 52 connected to the selected gate line 54. Meanwhile, the signal reading circuit 46 selects the signal lines 56 connected to the charge detecting circuits 57 one after another in the row direction of the TFT array in accordance with the timing control signals provided from the timing control circuit 48. As a result, the storage capacitor 53 of the pixel 50 corresponding to the selected gate line 54 and signal line 56 discharges the charge information associated with the piece of radiation image information $S_1$, and the image processor 20 receives this charge information as an image signal. After the image signal from each of the pixels 50 in the selected row has been read out, the gate line driving circuit 44 selects the next gate line 54 in the column direction and supplies the driving signal to the selected gate line 54. The signal reading circuit 46 then reads out image signals from the TFTs 52 connected to the selected gate line 54 in the same manner. By repeating the operation described above, the two-dimensional piece of radiation image information $S_1$ stored in the sensor substrate 38 is read out and provided to the image processor 20 (step S4).

Next, a second shot is captured by applying radiation X to the subject 12 through the fixation material 11 with the radiation source controller 16 controlling the tube voltage and tube current of the radiation source 14 in accordance with the second image capturing condition ($S_2$) (step S5). It should be noted that the second shot is performed immediately after the first shot by the use of the predetermined second image capturing condition ($S_2$). Therefore, motion artifacts caused by the movement of the subject 12 between the first and second shots do not occur.

The second shot radiation image information $S_2$ detected by the solid-state radiation detector 18 is read out in the same manner as the first shot radiation image information $S_1$ and provided to the image processor 20 (step S6).

The weighting coefficient α specified in the processing condition selected by the processing condition selector 26 from the processing condition memory 24 is provided to the image processor 20 (step S7).

The image processor 20 then calculates in step S8 a piece of radiation image information S from the pieces of radiation image information $S_1$ and $S_2$ supplied by the solid-state radiation detector 18 and the weighting coefficient α selected from the processing condition memory 24 using $$S=\alpha \cdot S_1+S_2$$

(step S8).

As already mentioned, if plaster is used as the fixation material 11, the radiation absorption characteristic of the fixation material 11 varies with time after the fixation material 11 was applied to the subject 12. Therefore, the weighting coefficient α may be defined as a function of time after application of the fixation material 11 to the subject 12, α(t), and the piece of radiation image information S may be computed as $$S=\alpha(t) \cdot S_1+S_2.$$

The resultant piece of radiation image information S is displayed on the display unit 28 by the display controller 30 (step S9). The display unit 28 displays a radiation image of the desired image capturing site obtained by computing the piece of radiation image information S in a way that takes into account the type of the fixation material 11 applied to the subject 12.

It should be noted that the present invention is not limited to the embodiment described above and various variations and modifications may be made without departing from the scope of the invention.

For example, instead of using two pieces of radiation image information $S_1$ and $S_2$ obtained by two shots, the resultant piece of radiation image information S may be generated from three or more pieces of radiation image information obtained by three or more shots under different image capturing conditions. For instance, when using three pieces of radiation image information $S_1$ to $S_3$, a resultant piece of radiation image information S may be computed as $$S=K_1 \cdot S_1+K_2 \cdot S_2+K_3 \cdot S_3+K_4$$

where $K_1$ to $K_4$ are coefficients depending on the weight coefficient for extraction of the image capturing site and the gradation characteristics of the images. Note that the equation above can be rewritten with coefficients β and γ as $$S=\beta \cdot S_1+\gamma \cdot S_2+S_3.$$

Incidentally, instead of a TFT device, such a device as a CCD (Charge Coupled Device), a CMOS (Complementary Metal Oxide Semiconductor) device or the like may be used for a solid-state radiation detector 18.

Instead of the solid-state radiation detector 18 that converts applied radiation X directly into charge information, a radiation detector may be employed, which converts radiation X into visible light by means of a scintillator, and then converts the visible light into charge information. Alternatively, an optical readout radiation detector may be utilized. The optical readout radiation detector stores radiation X as a latent image and allows the latent image to be read out as charge information when scanned with reading light. Another possibility is to employ a stimulable phosphor panel, which stores radiation energy in a phosphor and emits stimulated light of an intensity corresponding to the stored energy when irradiated with stimulating light such as a laser beam.

What is claimed is:

1. A radiation image processing apparatus for producing a piece of radiation image information of a desired image capturing site by processing a plurality of pieces of radiation image information that are obtained by irradiation of a subject with radiation of different energies, respectively, the apparatus comprising:

a radiation source for irradiating the subject with the radiation, the subject being applied with a fixation material;

a radiation source controller for controlling the radiation source in sequence in accordance with preset two different image capturing conditions;

a processing condition memory for storing a plurality of processing conditions, each including the two different image capturing conditions and an image processing condition that correspond to a type of the fixation material and an image capturing site;

a processing condition readout unit for reading out one of the processing conditions that correspond to the type of the fixation material with which the subject is applied and the image capturing site;

an image capturing condition setting unit for setting the two different image capturing conditions that correspond to the type of the fixation material and the image capturing site included in the read out one of the processing conditions to the radiation source controller, and making the radiation source controller control the radiation source in sequence in accordance with the two different image capturing conditions that correspond to the type of the fixation material and the image capturing site;

a radiation converting panel for receiving and converting the radiation that has passed through the fixation material and the subject into one of the pieces of radiation image information; and an image processor for processing two pieces of radiation image information that are provided by the radiation converting panel under the two different image capturing conditions in accordance with the image processing condition included in the read out one of the processing conditions.

2. The apparatus according to claim 1, wherein the fixation material comprises plaster or fiberglass.

3. The apparatus according to claim 1, wherein the image capturing conditions include a tube voltage and a tube current for the radiation source, the tube voltage and the tube current being determined in accordance with the type of the fixation material and the image capturing site.

4. The apparatus according to claim 1, wherein the image processing condition included in the processing condition includes a weighting coefficient for a weighted subtraction using the two pieces of radiation image information provided by the radiation converting panel under the two different image capturing conditions.

5. The apparatus according to claim 4, wherein the fixation material comprises plaster, and the weighting coefficient is defined as a function of time after application of the fixation material to the subject.

6. A radiation image processing method used in a radiation image processing apparatus for producing a piece of radiation image information of a desired image capturing site by processing a plurality of pieces of radiation image information that are obtained by irradiation of a subject with radiation of different energies, respectively, the radiation image processing apparatus comprising a radiation source for irradiating the subject with the radiation, the subject being applied with a fixation material, a radiation source controller for controlling the radiation source in sequence in accordance with preset two different image capturing conditions, a radiation converting panel for receiving and converting the radiation that has passed through the fixation material and the subject into one of the pieces of radiation image information, and a processing condition memory for storing a plurality of processing conditions, each including the two different image capturing conditions and an image processing condition that correspond to a type of the fixation material and an image capturing site, the method comprising the steps of:

reading out from the processing condition memory one of the processing conditions that correspond to the type of the fixation material with which the subject is applied and the image capturing site;

setting the two different image capturing conditions that correspond to the type of the fixation material and the image capturing site included in the read out one of the processing conditions to the radiation source controller, and controlling the radiation source in sequence in accordance with the two different image capturing conditions that correspond to the type of the fixation material and the image capturing site; and performing image processing of the two pieces of radiation image information that are provided by the radiation converting panel under the two different image capturing conditions in accordance with the image processing condition included in the read out one of the processing conditions.

7. The method according to claim 6, wherein the fixation material comprises plaster or fiberglass.

8. The method according to claim 6, wherein the image capturing conditions include a tube voltage and a tube current for the radiation source, the tube voltage and the tube current being determined in accordance with the type of the fixation material and the image capturing site.

9. The method according to claim 6, wherein the image processing includes performing a weighted subtraction using the two pieces of radiation image information provided by the radiation converting panel under the two different image capturing conditions, and the processing condition includes a weighting coefficient for the weighted subtraction.

10. The method according to claim 9, wherein the fixation material comprises plaster, and the weighting coefficient is defined as a function of time after application of the fixation material to the subject.

* * * * *